United States Patent [19]
Shaw et al.

[11] Patent Number: 5,688,654
[45] Date of Patent: Nov. 18, 1997

[54] GAB$_A$ A RECEPTOR SUBTYPES AND METHODS FOR SCREENING DRUG COMPOUNDS USING IMIDAZOQUINOXALINES AND PYRROLOPYRIMIDINES TO BIND TO GABA$_A$ RECEPTOR SUBTYPES

[75] Inventors: Kenneth Shaw, Weston; Alan Hutchison, Madison; Andrew Thurkauf, Danbury; John Tallman, Guilford, all of Conn.

[73] Assignee: Neurogen Corporation, Brandford, Conn.

[21] Appl. No.: 331,501

[22] PCT Filed: Apr. 30, 1993

[86] PCT No.: PCT/US93/03920

§ 371 Date: Oct. 28, 1994

§ 102(e) Date: Oct. 28, 1994

[87] PCT Pub. No.: WO93/22681

PCT Pub. Date: Nov. 11, 1993

Related U.S. Application Data

[63] Continuation of Ser. No. 876,050, Apr. 30, 1992, Pat. No. 5,597,920.
[51] Int. Cl.$^6$ .................. G01N 33/566; G01N 33/567
[52] U.S. Cl. .................. 435/7.21; 436/501; 436/504
[58] Field of Search .................. 435/7.21; 436/501, 436/504; 530/350, 839

[56] References Cited

U.S. PATENT DOCUMENTS

| | | | |
|---|---|---|---|
| 4,280,993 | 7/1981 | Braestrup et al. | 436/503 |
| 5,130,430 | 7/1992 | Shaw | 544/346 |
| 5,216,159 | 6/1993 | Thurkauf et al. | 544/250 |

OTHER PUBLICATIONS

Mohler et al, NATURE, 294, 763–765, 1981.

*Primary Examiner*—David Saunders
*Attorney, Agent, or Firm*—McDonnell Boehnen Hulbert & Berghoff

[57] ABSTRACT

Disclosed are methods for screening compounds for potential therapeutic activity based on selective binding to GABAa receptors, and where the methods employ compounds of formulas I and II shown herein.

9 Claims, 2 Drawing Sheets

Compound 1

Compound 2

Compound 3

Compound 4

Compound 5

Compound 6

Compound 7

GABA_A RECEPTOR SUBTYPES AND METHODS FOR SCREENING DRUG COMPOUNDS USING IMIDAZOQUINOXALINES AND PYRROLOPYRIMIDINES TO BIND TO GABA_A RECEPTOR SUBTYPES

This application is a national phase filed pursuant to 35 U.S.C. § 371 of International Application PCT/US93/03920, filed Apr. 30, 1993, published as WO93/03920 Nov. 11, 1993, which is a continuation of U.S. patent application Ser. No. 07/876,050, filed Apr. 30, 1992 and now U.S. Pat. No. 5,597,920.

BACKGROUND OF THE INVENTION

1. Field of the Invention

This invention relates to methods for screening drug compounds that bind to GABAa receptors. More specifically, it relates to the use of imidazoquinoxalines and imidazopyrimidines in such drug screening methods. It further relates to novel $GABA_a$ receptor subtypes which bind certain imidazoquinoxalines and imidazopyrimidines.

2. Description of the Related Art

γ-Aminobutyric acid (GABA) is regarded as one of the major inhibitory amino acid transmitters in the mammalian brain. Forty years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous mount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207:274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors: binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51. Mohler & Okada, 1977, Br. J. Psychiatry 133: 261–68). The average therapeutic doses of these drugs in man also correlate with potency at the GABAa family of receptors (Tallman et al. 1980, Science 207: 274–281.). Thus, a radioreceptor assay, using tritiated diazepam, can serve as a tool for the discovery of novel therapeutics at the GABAa receptor.

In 1978, it became clear that GABA and related analogs could interact at the low affinity (1 μM) GABA binding site to enhance the binding of benzodiazepines to the clonazepan-sensitive site (Tallman et at. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979. Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, Young et al. 1981, J. Pharmacol Exp. Ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites was demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8: 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schofield et al. 1988, Nature 328, 221–227; Garrett et al. BBRC 156, 1039–1045, 1989). A number of distinct cDNAs were identified as subunits of the GABAa receptor complex by cloning and expression. These are categorized into $\propto$, $\beta$, $\gamma$, $\delta$, $\epsilon$, and provide a molecular basis for the GABAa receptor heterogeneity and distinctive regional pharmacology (Shivers et al. 1990, Neuron 4, 919–928: Levitan et al. 1988, Nature 335, 76–79). The $\gamma$ subunit appears to enable drugs like benzodiazepines to modify the GABA responses (Pritchett et al. 1989, Nature 338, 582–585). The delta subunit is associated with GABAa receptors that do not respond to benzodiazepines but may respond to other related compounds (Shivers et al., 1989, op. cit.) The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). Although predictive about potency at a receptor, the receptor binding assay does not totally predict the precise biological activity of such compounds: agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, carbolines possess intrinsic activity of their own opposite to that of the benzodiazepines: they become known as inverse agonists.

In addition, a number of other specific antagonists of the benzodiazepine receptor were developed based on their ability to inhibit the binding of benzodiazepines. The best studied of these compounds is an imidazodiazepine. (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunlceler et al., 1981, Nature 290: 514–16; Darragh et al., 1983, Eur. J. Clin. Pharmacol. 14: 569–70). When a radiolabeled form of this compound was studied (Mohler & Richards, 1981,Nature 294: 763–65), it was demonstrated that this compound would interact with the same number of sites as the benzodiazepines and beta-carbolines, and that the interactions of these compounds were purely competitive. This compound was the ligand of choice for binding to GABAa receptors to discover older leads because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous. A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85. Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA [(Braestrup & Nielson 1981, Nature 294: 472–474)]. Thus, the GABA shift in a receptor binding assay in addition to high affinity predicts generally the expected behavioral properties of the compounds.

SUMMARY OF THE INVENTION

The present invention provides methods for screening drug compounds comprising the steps of:

(a) conducting in a reaction mixture a competition reaction between compounds of formulas I or II radiolabeled with tritium or an iodine isotope and the drug to be tested, for a GABAa receptor having a binding site for the compound of formula I or II;

(c) separating the GABAa receptor bound radiolabeled compound of formula I or II from the reaction mixture; and (b) measuring the radioactivity resulting from specific binding of the radiolabeled compound of formula I or II to the GABAa receptor.

where formulas I and II are

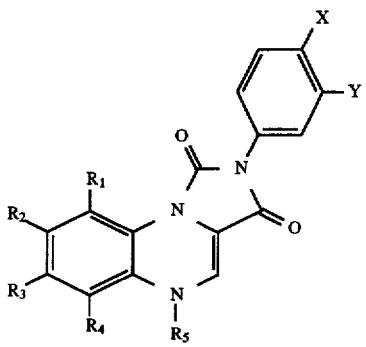

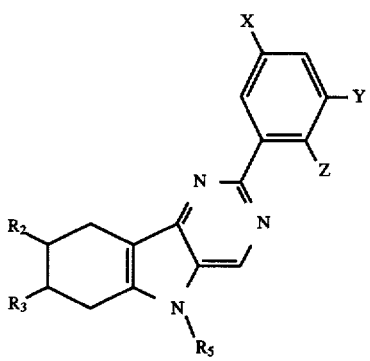

and the pharmaceutically acceptable salts thereof where:

R₁, R₂, R₃, and R₄ are the same or different and represent hydrogen, halogen, straight chain or branched lower alkyl having 1–6 carbon atoms, or straight chain or branched lower alkoxy having 1–6 carbon atoms;

R₅ is hydrogen or straight chain or branched lower alkyl, having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

The invention also provides tritium or iodine isotope radiolabeled compounds of the formulas

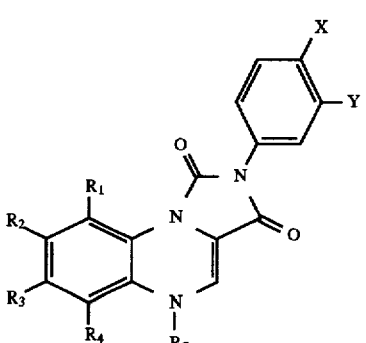

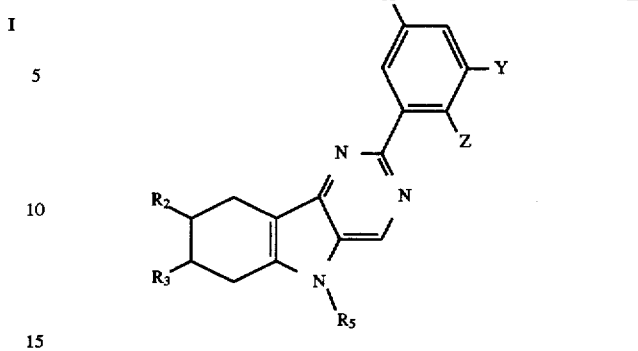

and the pharmaceutically acceptable salts thereof where:

R₁, R₂, R₃, R₄ are the same or different and represent hydrogen, halogen, straight chain or branched lower alkyl having 1–6 carbon atoms, or straight chain or branched lower alkoxy having 1–6 carbon atoms;

R₅ is hydrogen or straight chain or branched lower alkyl having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

Further, the invention provides novel GABAa receptor subtypes which specifically bind to compounds of formulas I or II.

The invention also provides GABAa receptor subtypes which are bound in situ to a compound of formula I or II.

The invention provides compounds and methods which can be utilized to discover and develop novel therapeutic agents useful in treating anxiety, sleep and seizure disorders and enhancing alertness. The compounds provided herein bind selectively to a novel subtype of the GABAa binding site. This novel subtype is a subset of GABAa receptors which is distinct from those GABAa receptors disclosed in the prior art. Selective interaction of ligands at this unique receptor population results in pharmacological specificity which may lead to superior anxiolytics, cognition enhancers, anticonvulsants and sedative hypnotics.

DETAILED DESCRIPTION OF THE INVENTION

The present invention provides methods for screening drug compounds comprising the steps of:

(a) conducting in a reaction mixture a competition reaction between compounds of formulas I or II radiolabeled with tritium or an iodine isotope and the drug to be tested, for a GABAa receptor having a binding situ for the compound of formula I or II;

(c) separating the GABAa receptor bound radiolabeled compound of formula I or II from the reaction mixture; and (b) measuring the radioactivity resulting from specific binding of the radiolabeled compound of formula I or II to the GABAa receptor.

where formulas I and II are

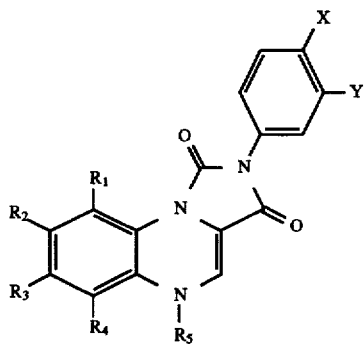

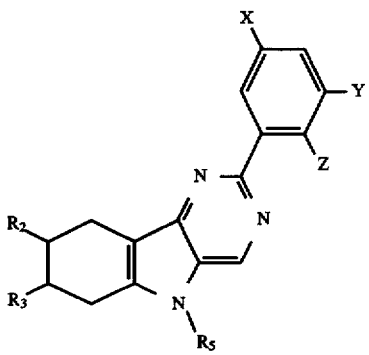

and the pharmaceutically acceptable salts thereof where:

$R_1$, $R_2$, $R_3$, and R4 are the same or different and represent hydrogen, halogen, straight chain or branched lower alkyl having 1–6 carbon atoms, or straight chain or branched lower alkoxy having 1–6 carbon atoms;

$R_5$ is hydrogen or straight chain or branched lower alkyl having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

The invention also provides tritium or iodine isotope radiolabeled compounds of the formulas

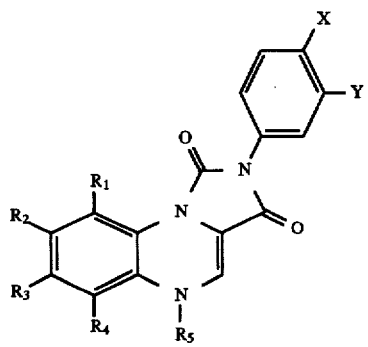

and

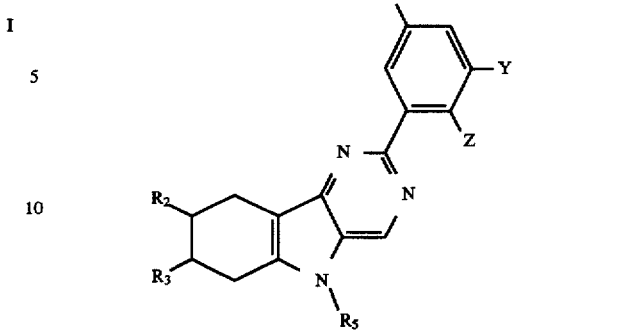

and the pharmaceutically acceptable salts, thereof where:

$R_1$, $R_2$, $R_3$, $R_4$ are the same or different and represent hydrogen, halogen, straight chain or branched lower alkyl having 1–6 carbon atoms, or straight chain or branched-lower alkoxy having 1–6 carbon atoms;

$R_5$ is hydrogen or straight chain or branched lower alkyl having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

Further, the invention provides novel GABAa receptor subtypes which specifically bind to compounds of formulas I or II.

The invention also provides GABAa receptor subtypes which are bound in situ to a compound of formula I or II.

Figure 1A:
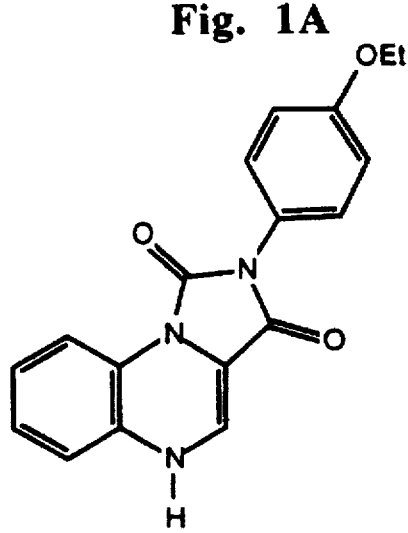
FIGS. 1A–G show representative imidazoquinoxalines and imidazopyrimidines which are employed in the methods of the present invention.
Figure 1B:
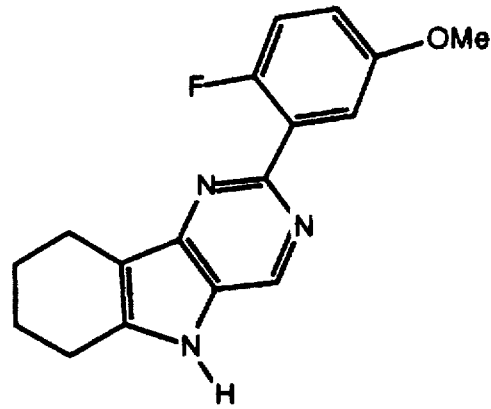
Figure 1C:
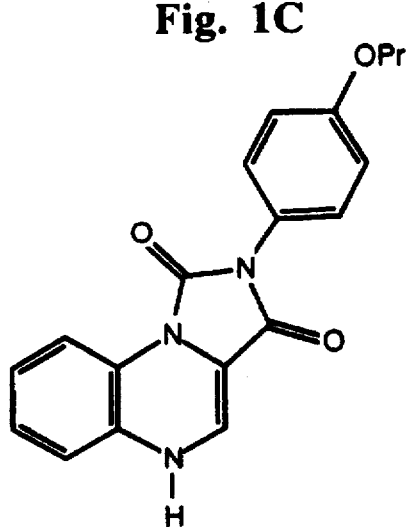
Figure 1D:
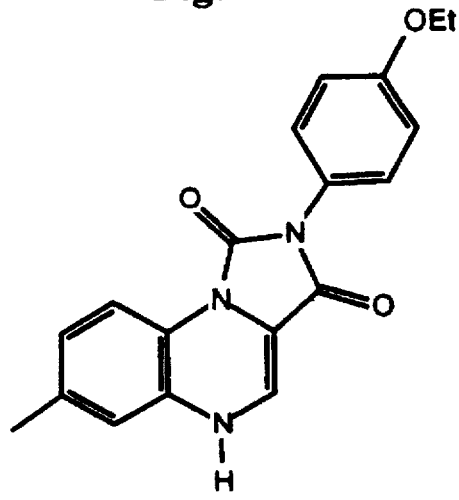
Figure 1E:
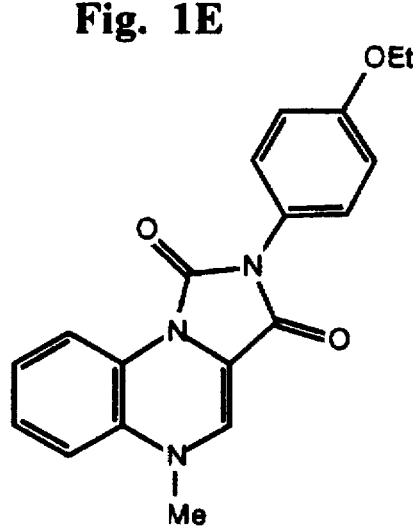
Figure 1F:
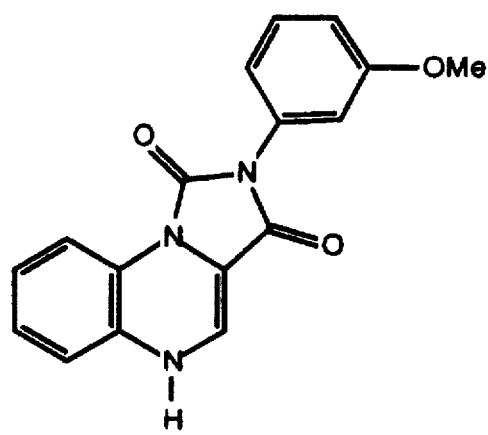
Figure 1G:
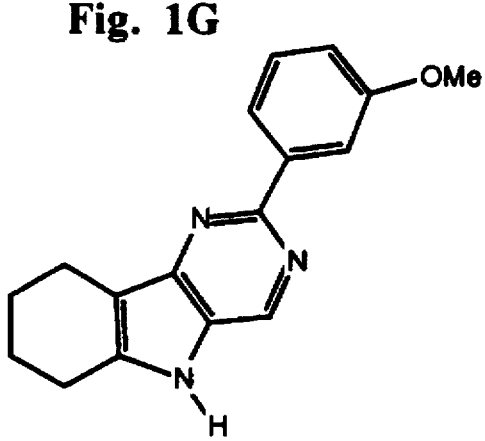

Representative compounds suitable for use in the drug screening methods of the present invention, which are encompassed by formulas I and II include, but are not limited to, the compounds in FIGS. 1A–G and their pharmaceutically acceptable salts.

The compounds which may be employed in the inventive methods may be radiolabeled with any convenient radiolabel. Such radiolabels are, for example, isotopes of hydrogen, carbon, and iodine. A convenient hydrogen isotope is tritium. The compounds may also be prepared to include various isotopes of iodine, such as, for example, $^{127}$I. The suitable isotopes of carbon are $^{13}$C and $^{14}$C.

The invention provides compounds and methods which can be utilized to discover and develop novel therapeutic agents useful in treating anxiety, sleep and seizure disorders and enhancing alertness. The compounds provided herein bind selectively to a novel subtype of the GABAa binding site. This novel subtype is a subset of GABAa receptors which is distinct from those GABAa receptors disclosed in the prior art. Selective interaction of ligands at this unique receptor population results in pharmacological specificity which may lead to superior anxiolytics, cognition enhancers, anticonvulsants and sedative hypnotics.

Prior art compounds known to have high affininty for all GABAa receptors did not exhibit such affinity for the receptor of the present invention. The prior art compounds all demonstrated low affinity towards the novel receptor subtypeof the invention. Table II below shows the affinities of prior art compounds towards known GABAa receptors. These data indicate that one skilled in the art would have expected those compounds to have similar affinities towards the GABAa receptor of the present invention. The data presented in Tables I and II clearly indicate that the prior art compounds have dramatically lower affinities towards the novel receptor subtype.

An illustration of the preparation of compounds of the present invention is given in Schemes I and II. Those having skill in the art will recognize that the starting materials may be varied and additional steps employed to produce either tritiated or iodinated compounds encompassed by the present invention, as demonstrated by the following examples.

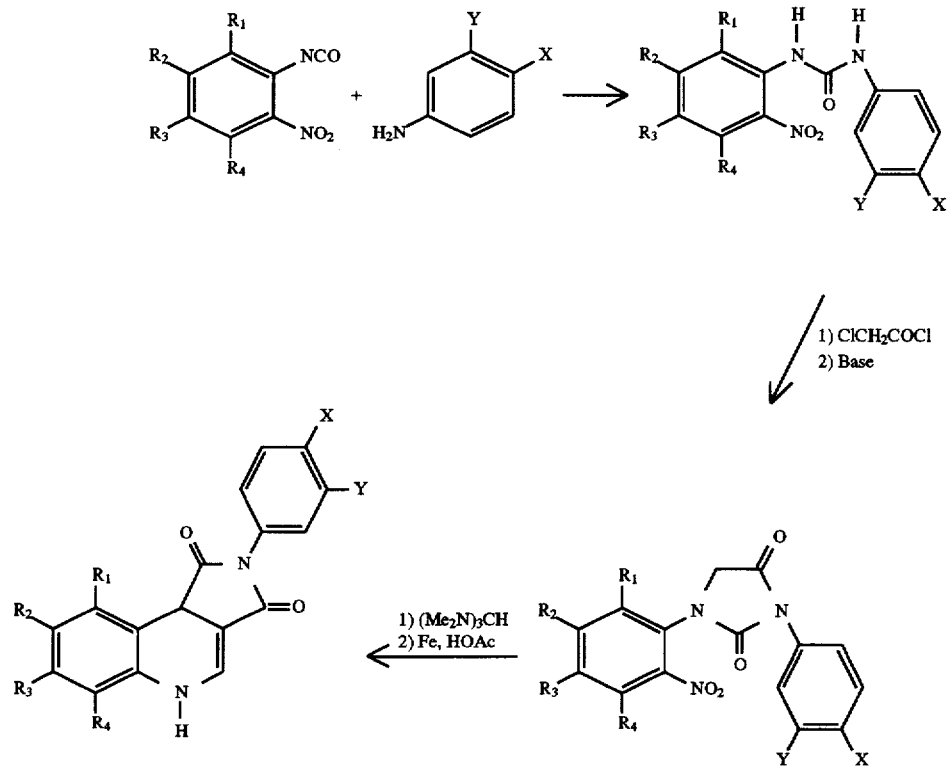

Scheme I

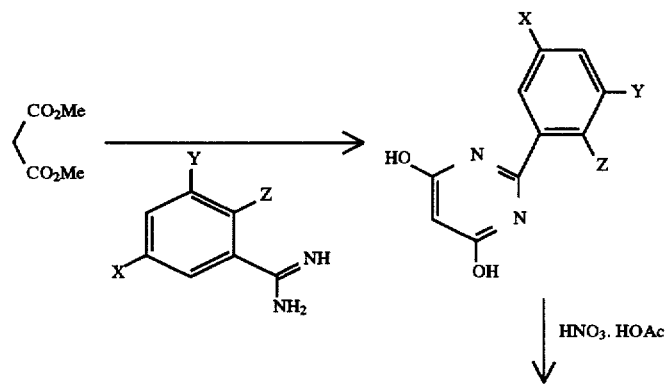

Scheme II

-continued
Scheme II

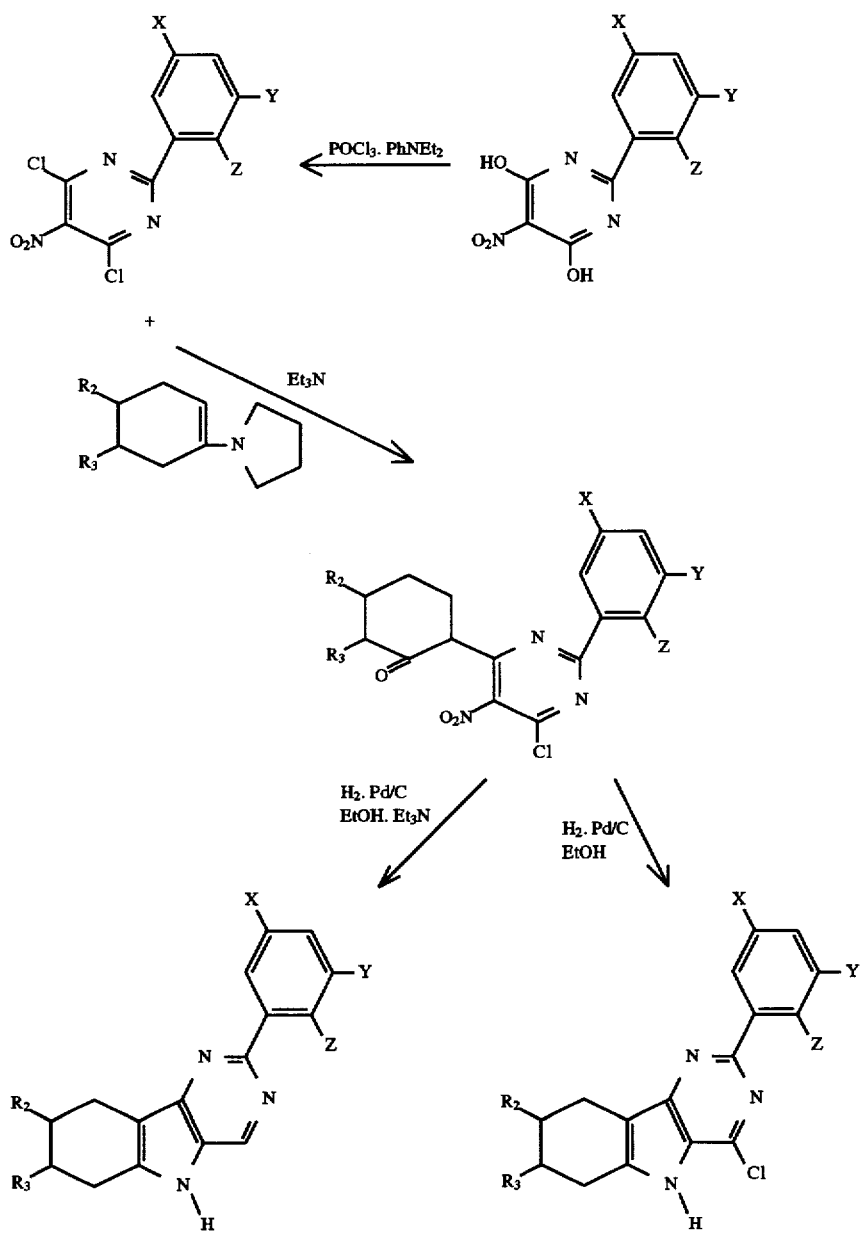

wherein:

$R_1$, $R_2$, $R_3$, and $R_4$ are the same or different and represent hydrogen, halogen, straight chain or branched lower alkyl having 1–6 carbon atoms, or straight chain or branched lower alkoxy having 1–6 carbon atoms;

$R_5$ is hydrogen or straight chain or branched lower alkyl having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

The methods for drug screening of the present invention are competitive assays where two compounds, one of which is radiolabeled, compete for a GABAa receptor. In these methods, either of the compounds of formulas I and II may be radiolabeled or the drug to be tested may be radiolabeled. Preferred methods are those in which a compound of formula I or II is radiolabeled and allowed to compete for a GABAa receptor.

The invention is illustrated further by the following examples which are not to be construed as limiting the invention in scope or spirit to the specific procedures and compounds described in them.

EXAMPLE 1

Drug Screening Assay

The methods for screening drug compounds of the invention using the novel GABAa receptor are illustrated by the following assays for GABAa receptor subtype activity.

Assays were carried out using the tissue preparation described in Thomas and Tallman (J. Bio. Chem. 156:

9838–9842, 1983, J. Neurosci 3: 433–440, 1983). Rat cortical tissue was dissected and homogenized in 25 volumes (w/v) of 0.05M Tris HCl buffer (pH 7.4 at 4° C.). The tissue homogenate was centrifuged in the cold (4°) at 20,000×g for 20'. The supernatant was decanted and the pellet was rehomogenized in the same volume of buffer and again centrifuged at 20.000×g. The supernatant was decanted and the pellet was frozen at −20° C. overnight. The pellet was then thawed and rehomogenized in 25 volume (original wt/vol) of buffer and the procedure was carried out twice. The pellet was finally resuspended in 50 volumes (w/vol of 0.05M Tris HCl buffer containing 1 uM Ro 15-1788, 1 uM sodium ascorbate and 10 uM muscimol (pH 7.4 at 4° C.).

Incubation mixtures contained 400 µl of tissue homogenate. 5µl of 100 nM ligand in above buffer [final ligand concentration was 0.5 nM $^3$H-Compound 1 (specific activity 67 Ci/mmol)], drug or blocker and buffer to a total volume of 1 ml. Incubations were carried for 20 min at 4° C. then were rapidly filtered through GFB filters to separate free and bound ligand. Filters were washed twice with fresh 0.05M Tris HCl buffer (pH 7.4 at 4° C.) and counted in a liquid scintillation counter. 10 µM Compound 3 was added to some tubes to determine nonspecific binding. Data were collected in triplicate determinations, averaged and % inhibition of total specific binding was calculated. Total Specific Binding=Total−Nonspecific. Typically the specific binding represented about 75 to 85% of total binding. In some cases, the amounts of unlabeled drugs was varied and total displacement curves of binding were carried out. Data were convened to a form suitable for the calculation of $IC_{50}$ and Hill Coefficient ($n_H$). These IC 50's were convened to Ki's using the Cheng Prusoff equation (Cheng and Prussoff, 1973, Biochem. Pharmacol. 22: 3099.). Data for the compounds of this invention as well as certain reference compounds are listed in Table I. All of the reference prior art compounds tested demonstrated low affinity for this receptor subtype.

TABLE I

| Compound Name or Number[1] | Ki (nM) |
|---|---|
| Alprazelam | 8000 |
| Diazepam | 5000 |
| Flumazenil | 7500 |
| Bretazenil | 15000 |
| Zolpidem | 2200 |
| Compound 1 | 0.5 |
| Compound 2 | 3.9 |
| Compound 3 | 0.9 |
| Compound 4 | 0.5 |
| Compound 5 | 6 |
| Compound 6 | 0.55 |
| Compound 7 | 50 |

[1]Compound numbers relate to compounds of the present invention shown in FIGS. 1A–G.

Table II lists the affinities of prior art compounds for known GABAa receptors.

TABLE II

| Compound Name | Ki (nM) |
|---|---|
| Diazepam | 6 |
| Flumazenil | 1 |
| Bretazenil | 1 |
| Zolpidem | 20 |

Examples II–XIII are syntheses of the compounds of the invention.

EXAMPLE II

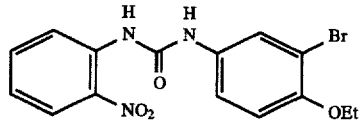

To a solution of 2-Nitrophenyl isocyanate (3.34 g) in 100 mL of toluene was added 3-Bromo-4-ethoxyaniline (3.1 g). The mixture was stirred at 20° C. for 30 min. Hexane (300 mL) was added and the resulting solid was filtered and dried to yield N-(2-Nitrophenyl)-N'-(3-bromo-4-ethoxyphenyl)-urea as a light yellow solid.

EXAMPLE III

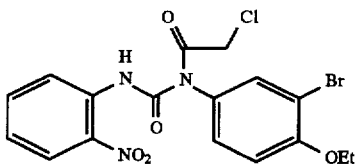

A solution containing N-(2-Nitrophenyl)-N'-(3-bromo-4-ethoxyphenyl)-urea (5.76 g) and chloroacetyl chloride (413 mL) was refluxed under nitrogen for 30 min. After the excess chloroacetyl chloride was removed in vacuo, diethyl ether (50 mL) was added and the resulting solid was filtered and dried to yield N'-(2-chloroacetyl)-N-(2-nitrophenyl)-N'-(3-bromo-4-ethoxyphenyl)-urea as a white solid.

EXAMPLE IV

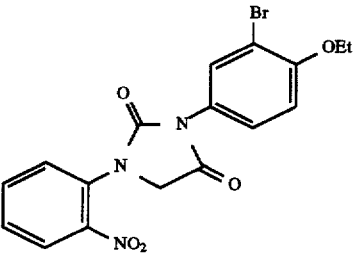

A solution of N'-(2-Chloroacetyl)-N-(2-nitrophenyl)-N'-(3-bromo-4-ethoxyphenyl)-urea (3.7 g), dimethylformamide (15 mL) and diisopropyl-ethylamine (15 mL) was refluxed for 5 min. The hot mixture was allowed to cool to room temperature and precipitated by adding the mixture to 200 mL of water. The precipitate was collected and dried to yield 1-(2-Nitrophenyl)-3-(3-bromo-4-ethoxyphenyl)-imidazoline-2,4(1H,3H)-dione.

EXAMPLE V

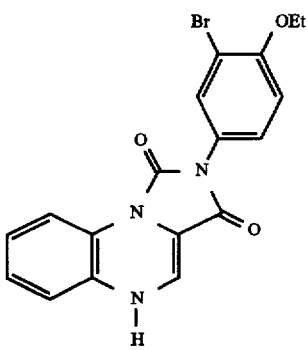

To a solution containing 1 -(2-Nitrophenyl)-3-(3-bromo-4-ethoxy-phenyl)-imidazoline-2,4( 1H,3H)-dione ( 1.18 g) in anhydrous methylene chloride (5 mL) under nitrogen was added tris(dimethylamino)methane (1 mL). The reaction was stirred at room temperature for 20 min and the solvent was removed in vacuo. To the resulting oil was added iron powder (5 g) and acetic acid (250 mL). This mixture was carefully heated to reflux for 3 min followed by stirring the reaction for an additional 30 min. The heterogeneous mixture was diluted with 10% methanol-methylene chloride (200 mL) and filtered through silica gel using 10% methanol/methylene chloride as eluant. The solvent was removed in vacuo and hot ethanol (200 mL) was added. To this mixture was added water (200 mL) and the resulting solid was filtered and washed successively with ethanol, ethyl acetate, diethyl ether and dried to yield 2-(3-Bromo-4-ethoxyphenyl)-imidazo[1,5-a]quinoxaline- 1,3(2H,5H)-dione as a yellow solid.

EXAMPLE VI

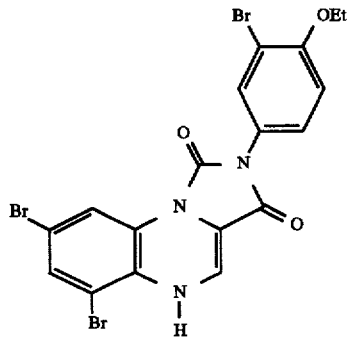

To 2-(3-Bromo-4-ethoxyphenyl)-imidazo{1,5,a}quinoxaline-1,3(2H,5H)-dione (250 mg) in dioxane (10 mL) was added Bromine (1 mL). The reaction mixture was heated to 80° C. for 1.5 hr and theft poured directly into a suspension of zinc dust (2.0 gm) in acetic acid (50 mL). The reaction mixtture was heated to reflux for 5 min and then allowed to cool to room temperature over 45 min. The suspension was filtered through celite and evaporated under reduced pressure. The resulting solid was stirred for 10 min with a solution containing ethanol (25 mL) and water (50 ml) and filtered. The solid was washed with ethanol (10 mL) followed by ether (10 mL) to yield 6,8-Dibromo-2-(3-Bromo-4-ethoxyphenyl)-imidazo[1,5,a]quinoxaline-1,3(2H,5H)-dione as a yellow solid.

EXAMPLE VII

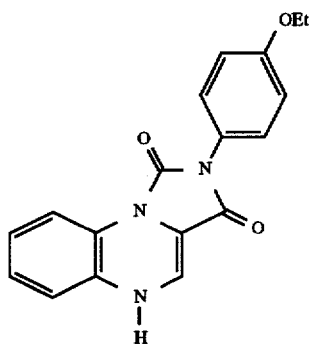

Compound 1

6,8-Dibromo-2-(3-Bromo-4-ethoxyphenyl)-imidazo[1,5,a]quinoxaline-1,3(2H,5H)-dione (7.5 mg) dissolved in a suspension containing dimethylformamide (1 mL), absolute ethanol (1 mL), triethylamine (10 ul) and 10% palladium on carbon (5 mg) was stirred under tritium gas at atmospheric pressure for 30 min. The reaction vessel was degassed, filtered through celite and the solvent was removed at reduced pressure. The reaction mixture was then subjected to three ethanol (3 mL) and one acetic acid (3 mL) dissolution-evaporation cycles to eliminate all radioactive exchangable protons. The desired tritiated 2-(4-Ethoxyphenyl)imidazo[1,5,a]quinoxaline- 1,3(2H,5H)-dione (Compound 1) was purified by preparative HPLC. It had Specific Activity of 67 Ci/mmol.

EXAMPLE VIII

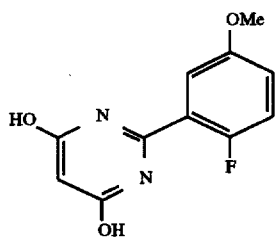

A mixture of 2-Fluoro-5-methoxybenzamidine (10.3 g) and dimethyl malonate (8.09 g) in dry dimethyl sulfoxide (7 mL) was allowed to stand at room temperature for 24 h. The precipitated product was collected and washed with water and ether to afford 2-Phenyl-4,6-dihydroxy-pyrimidine as a white solid.

EXAMPLE IX

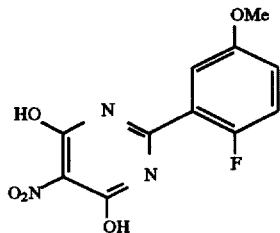

To a suspension of 2-(2-Fluoro-5-methoxyphenyl)-4,6-dihydroxy-pyrimidine (12 g) in 35 mL of acetic acid is added 12 mL of 90% nitric acid and the mixture is heated at 50° C. for 45 min. The reaction mixture is diluted with 150 mL of water and the product is collected, washed with water and ethanol and oven dried to afford 2-(2-Fluoro-5-methoxyphenyl)-5-nitro-4,6-dihydroxy-pyrimidine as a pink solid.

EXAMPLE X

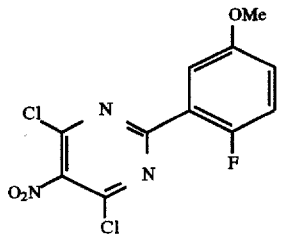

A mixture of 2-(2-Fluoro-5-methoxyphenyl)-5-nitro-4,6-dihydroxy-pyrimidine (10 g), diethylaniline (7 g) and phosphorus oxychloride (100 mL) was heated at reflux for 40 min. The reaction mixture was concentrated in vacuo and the residue was partitioned between 50% ether in ethyl acetate and water. The organic layer was dried over magnesium sulfate and the solvent was removed in vacuo. The residue was filtered through silica gel with ether/methylene chloride as the eluent to afford 2-(2-Fluoro-5-methoxyphenyl)-5-nitro-4,6-dichloro-pyrimidine as a yellow solid.

EXAMPLE XI

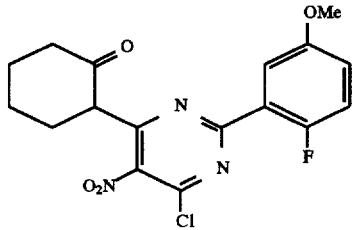

A mixture of cyclohexanone (98 mg) and pyrrolidine (71 mg) and 4A molecular sieves (500 mg) in 1 mL of benzene is allowed to stand at room temperature until enamine formation was complete (ca. 16 h). The resulting solution of enamine was cannulated into a solution of 2-(2-Fluoro-5-methoxyphenyl)-5-nitro-4,6-dichloro-pyrimidine (300 mg) and diisopropylethylamine (129 mg) in 5 mL of methylene chloride. After 30 min at room temperature the reaction mixture was concentrated in vacuo and treated with 3 mL of 3N HCl and 3 mL of ethanol. The reaction mixture was concentrated again and the residue was subjected to flash chromatography on silica gel with 20% ethyl acetate/hexane as the eluent to afford 2-[4-(2-(2-Fluoro-5-methoxyphenyl)-5-nitro-6-chloro-pyrimidinyl)]-cyclohexan-1-one as a white solid.

EXAMPLE XII

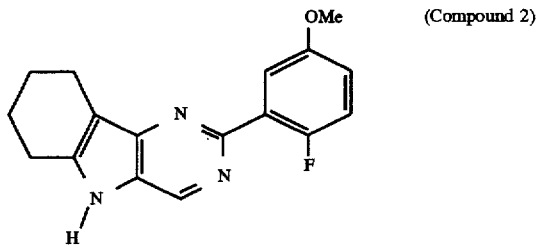

(Compound 2)

A mixture of 2-[4-(2-(2-Fluoro-5-methoxyphenyl)-5-nitro-6-chloro-pyrimidinyl)]-cyclohexan-1-one (280 mg), triethylamine (300 mg) and 10% Pd/C catalyst (25 mg) in 10 mL of ethanol was hydrogenated under 1 atmosphere of hydrogen at room temperature for 16 h. After filtration through celite the solvent was removed in vacuo and the residue was subjected to flash chromatography on silica gel with 50% ethyl acetate/hexane as the eluent to afford 2-(2-Fluoro-5-methoxyphenyl)-6,7,g,9-tetrahydro-5H-indolo[3,2-d]-pyrimidine melting at 197°–198° C. (Compound 2) after trituration with hexane/ether. Performing essentially the same procedure with tritium gas afforded tritiated 2-(2-Fluoro-5-methoxyphenyl);6,7,8,9-tetrahydro-5H-indolo[3.2-d]-pyrimidine (Compound 2).

EXAMPLE XIII

The following compounds were prepared essentially according to the procedures described in Examples I–XI.

a) 2-(4-Propyloxyphenyl)imidazo[1,5,a]quinoxaline-1,3 (2H,5H)-dione (Compound 3).

b) 2-(4-Ethoxyphenyl)-7-methyl-imidazo[1,5,a] quinoxaline-1,3(2H,5H)-dione (Compound 4).

c) 2-(4-Ethoxyphenyl)-5-methyl-imidazo[1,5,a] quinoxaline-1,3(2H,5H)-dione (Compound 5).

d) 2-(3-Methoxyphenyl)imidazo[1,5,a]quinoxaline-1,3 (2H,5. H)-dione (Compound 6).

e) 2-(3-Methoxyphenyl)-6,7,8,9-tetrahydro-5H-indolo [3.2-d]-pyrimidine (Compound 7).

The invention and the manner and process of making and using it, are now described in such full clear, concise and exact terms as to enable any person skilled in the art to which it pertains, to make and use the same. It is to be understood that the foregoing describes preferred embodiments of the present invention and that modifications may be, made therein without departing from the spirit or scope of the present invention as set forth in the claims. To particularly point out and distinctly claim the subject matter regarded as invention, the following claims conclude this specification.

What is claimed is:

1. A method of screening compounds for potential therapeutic activity comprising;

(a) adding flumazenil to a preparation containing GABAa receptors to allow the flumazenil to bind to GABAa receptors;

(b) utilizing the resulting treated preparation from (a) in a reaction mixture for conducting a competition reaction between a compound of Formula (I) or (II) radiolabeled with tritium or an iodine isotope and the compound to be screened for remaining GABAa receptors, to which flumazenil has not bound but which have a specific binding site for a compound of formula I or II;

(c) separating the GABAa receptor bound radiolabeled compound of formula I or II from the reaction mixture of (b); and (d) measuring the radioactivity resulting from specific binding of the radiolabeled compound of formula I or II to the remaining GABAa receptors, where formulae I and II are

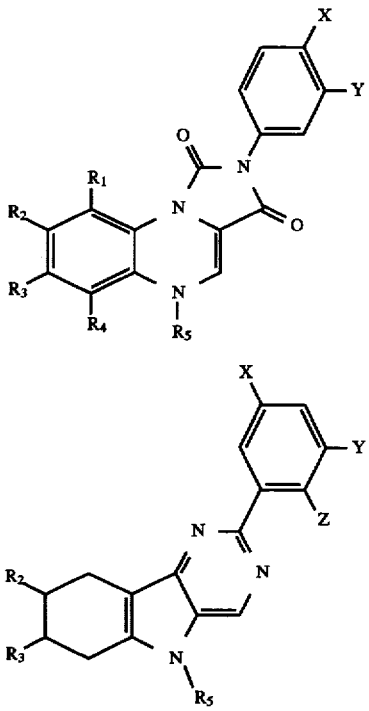

and the pharmaceutically acceptable salts thereof wherein:

$R_1$, $R_2$, $R_3$, $R_4$ independently represent hydrogen, halogen, straight chain or branched lower alkyl having 1–6 carbon atoms, or straight chain or branched lower alkoxy having 1–6 carbon atoms;

$R_5$ is hydrogen or straight chain or branched lower alkyl having 1–6 carbon atoms;

X and Y are the same or different and represent hydrogen, halogen, straight chain or branched lower alkyl having 1–6 carbon atoms, or straight chain or branched lower alkoxy having 1–6 carbon atoms; and Z is hydrogen or fluorine.

2. A method according to claim 1, where the compound is 2-(4-Ethoxyphenyl)imidazo[1,5-a]quinoxaline-1,3-(2H, 5H)-dione.

3. A method according to claim 1, where the compound is 2-(2-Fluoro-5-methoxyphenyl)-6,7, 8,9-tetrahydro-5H-indolo-[3,2-d]pyrimidine.

4. A method according to claim 1, where the compound is 2-(4-propyloxyphenyl)imidazo[1,5-a]quinoxaline-1,3 -(2H, 5H)-dione.

5. A method according to claim 1, where the compound is 2-(4-Ethoxyphenyl)-7-methyl-imidazo [1,5 -a]quinoxaline-1,3-(2H,5H)-dione.

6. A method according to claim 1, where the compound is 2-(4-Ethoxyphenyl)-5-methyl-imidazo [1,5-a]quinoxaline-1,3-(2H,5H)-dione.

7. A method according of claim 1, where the compound is 2-(3-Methoxyphenyl)imidazo[1,5-a]quinoxaline-1,3-(2H, 5H)-dione.

8. A method according to claim 1, where the compound is 2-(3-Methoxyphenyl)6,7,8,9-tetrahydro-5H-indolo-[3,2-d]pyrimidine.

9. A method according to claim 1, where the compound is 6,8-Dibromo-2-)3-bromo-4-ethoxyphenyl)imidazo([1,5-a] aquinoxaline-1,3-(2H,5H)-dione.

* * * * *